United States Patent
Wojcieszak et al.

(10) Patent No.: US 9,351,666 B2
(45) Date of Patent: May 31, 2016

(54) ANTHROPOMETRIC MEASURING DEVICE

(71) Applicant: Wolverine World Wide, Inc., Rockford, MI (US)

(72) Inventors: Craig M. Wojcieszak, Medford, MA (US); Matthew F. Teleen, Arlington, MA (US)

(73) Assignee: Wolverine World Wide, Inc., Rockford, MI (US)

( * ) Notice: Subject to any disclaimer, the term of this patent is extended or adjusted under 35 U.S.C. 154(b) by 155 days.

(21) Appl. No.: 14/159,639

(22) Filed: Jan. 21, 2014

(65) Prior Publication Data
US 2015/0201866 A1    Jul. 23, 2015

(51) Int. Cl.
| | |
|---|---|
| G01B 3/10 | (2006.01) |
| A61B 5/107 | (2006.01) |
| A43D 1/02 | (2006.01) |
| A61B 5/00 | (2006.01) |
| G01B 3/00 | (2006.01) |

(52) U.S. Cl.
CPC .............. *A61B 5/1074* (2013.01); *A43D 1/02* (2013.01); *A61B 5/6829* (2013.01); *G01B 3/004* (2013.01); *G01B 3/10* (2013.01)

(58) Field of Classification Search
CPC ...... G01B 11/022; G01B 11/24; G01B 3/004; G01B 3/10; A61B 2562/0219; A61B 5/1116; A61B 5/7264; A61B 5/7282
USPC ........................................... 33/512, 755–771
See application file for complete search history.

(56) References Cited

U.S. PATENT DOCUMENTS

| | | | |
|---|---|---|---|
| 650,389 A | 5/1900 | Hatfield | |
| 4,433,486 A | 2/1984 | Muehlenbein | |
| 4,875,296 A * | 10/1989 | Holzmeister | G01B 5/025 33/2 R |
| 4,878,271 A * | 11/1989 | Kitokovsky | A44B 11/10 24/194 |
| 4,920,659 A | 5/1990 | Becher | |
| 5,406,715 A * | 4/1995 | Koizumi | G01B 3/1002 33/512 |

(Continued)

FOREIGN PATENT DOCUMENTS

| | | |
|---|---|---|
| AU | 2002322200 B2 | 12/2006 |
| DE | 1052696 | 3/1959 |

OTHER PUBLICATIONS

Extended European Search Report, Application No. 14171060, dated Sep. 22, 2014.

(Continued)

*Primary Examiner* — Yaritza Guadalupe-McCall
(74) *Attorney, Agent, or Firm* — Warner Norcross & Judd LLP (57) ABSTRACT

A measuring device with a measuring tape and a one-piece handle. The handle includes a main body with a fixed reference, an anchor portion with a movable reference and a resilient element. The measuring tape is secured to the anchor portion. The resilient element allows the anchor portion to move with respect to the main body when the measuring tape is under the tension. The resilient element is configured so that the movable reference comes into alignment with the fixed reference when the measuring tape is under proper tension. The fixed reference may also provide a reference from which to take measurements. The resilient element may include a pair of nonlinear segments that straighten under tension. The main body may include a pair of fixed references disposed on opposite sides of the measuring tape, and the anchor portion may include a pair of corresponding movable references.

25 Claims, 7 Drawing Sheets

(56) References Cited

U.S. PATENT DOCUMENTS

| | | | | |
|---|---|---|---|---|
| 5,732,475 A * | 3/1998 | Sacks | ............... | G01B 5/30 33/512 |
| 5,813,132 A * | 9/1998 | Bodkin, Sr. | ............... | G01B 5/061 33/494 |
| 6,640,460 B1 * | 11/2003 | Nabarro | ............... | G01B 3/1002 33/512 |
| 7,617,615 B1 * | 11/2009 | Martorell | ............... | G01B 3/1061 33/511 |
| 8,141,266 B2 * | 3/2012 | Sun | ............... | G01B 3/08 33/755 |
| 8,303,327 B1 * | 11/2012 | Sun | ............... | H01R 13/639 439/369 |
| 8,601,709 B2 * | 12/2013 | Sun | ............... | G01B 7/02 33/755 |
| 2011/0247179 A1 | 10/2011 | Bellamy et al. | | |
| 2012/0085277 A1 * | 4/2012 | Abdel-Rahman | ............... | A61B 5/1072 116/201 |
| 2015/0201866 A1 * | 7/2015 | Wojcieszak | ............... | G01B 3/10 33/512 |

OTHER PUBLICATIONS

The Brannock Device Co., Inc. website, believed to be published at least as early as Jan. 20, 2014.

* cited by examiner

ANTHROPOMETRIC MEASURING DEVICE

BACKGROUND OF THE INVENTION

The present invention relates to measuring devices and more particularly to measuring devices that operate under tension.

Anthropometric measuring devices are often used to measure the dimension of various parts of the human body. For example, anthropometric measuring devices can be used to measure foot circumference for use in determine footwear width or can be used to measure chest circumference for use in determining coat or shirt size. A typical anthropometric measuring device includes a flexible measuring tape that is graduated in essentially the same manner as a ruler. In use, the flexible measuring tape can be wrapped circumferentially around the part to be measured and then back onto itself to provide the measurement. In many anthropometric applications, the body part being measured will have relatively soft tissue that can be compressed if the measuring tape is wrapped under tension. This means that the circumferential measurement can vary with the amount of tension applied to the measuring tape.

To address this issue and provide uniform measurement, anthropometric measuring devices have been developed that assist a user in taking measurements under uniform tension. For example, one conventional device includes a multiple-piece tension measuring device that is fixed to the free end of a measuring tape. The measure tape is spooled onto a reel. In use, the user extends the measuring tape from the reel and pulls the tension measuring device to apply tension to the measuring tape. To take a measurement, the user wraps the measuring tape around the body part and applies increasing tension while watching the tensioning measuring device. This requires the user to focus on the scale of the tension measuring device. When the proper tension is achieved, the user must change focus from the tension measuring device to the measuring tape to read the measuring tape measurement. This creates some difficulty as it is possible that the tension will change while the user is moving focus from the tension measuring device scale to the measuring tape graduations. In addition to presenting practical difficulties in use, the tension measuring device is relatively complex having a plurality of different parts that are separately manufactured and assembled to form the complete unit.

SUMMARY OF THE INVENTION

The present invention provides an anthropometric measuring device with a measuring tape and a one-piece handle. The one-piece handle includes a fixed reference, a movable reference and at least one resilient element that allows the movable reference to move when the measuring tape is subjected to tension. The resilient element is configured to allow the movable reference to move into alignment with the fixed reference when the measuring tape is under the proper tension. The resilient element is configured to remain within its elastic deformation range when subjected to the anticipated range of forces, which typically will include the desired tension plus an additional amount to allow for some overshoot when applying tension to the measuring tape. This allows the resilient element to return to its original shape and provides uniformity of result during repeated uses.

In one embodiment, the resilient element includes a pair of nonlinear segments that are configured to increasingly straighten under increasing tension. The straightening of the nonlinear segment extends the effective length of the resilient element, thereby providing movement of the movable reference with respect to the remainder of the handle.

In one embodiment, the handle includes two resilient elements and an anchor bar that bridges the free ends of the two resilient elements. In this embodiment, the resilient elements are nonlinear and movement of the anchor bar may be achieved by pulling on the measuring tape with sufficient force to increasingly straighten the resilient elements. In one embodiment, each resilient element follows a sinusoidal shape when relaxed.

In some embodiments, the device includes a movable indicator disposed on one end of the anchor bar. In other embodiments, the anchor bar includes two movable indicators, one disposed on each end of the anchor bar. The movable indicator (or indicators) may be pointers protruding from the anchor bar in a direction substantially perpendicular to the longitudinal extent of the measuring tape.

In some embodiments, the device includes a fixed reference that is supported by an arm extending from the main body of the handle. The arm may include an indicator that cooperates with the movable reference to present a visual indication when the measuring tape is under proper tension. In other embodiments, the device includes two fixed references that are supported by different arms extending from the main body of the handle. Each arm may include an indicator. The arms may be configured so that the fixed indicators are disposed on opposite sides of the measuring tape, thereby providing opposed indicators that can help to ensure that the measuring tape is pulled straight and not on an angle with respect to the handle.

The present invention provides a simple and effective measuring device well-suited for use in taking anthropometric circumferential measurements. The one-piece handle is inexpensive to manufacture and easy to use. The use of resilient elements that are maintained within their elastic deformation range provides uniform measurements over repeated uses. The use of a single fixed reference for tension and size eliminates the need to change focus between tension measurements and size measurements. Instead, the user can see the tension reference and the measurement markings simultaneously. This makes it easy to use the present invention and helps to ensure more accurate measurements. When included, opposed fixed indicators help to ensure that tension is applied in alignment with the longitudinal extent of the measuring tape. This can be particularly beneficial in applications with two resilient elements, as it may help to ensure relatively uniform application of force to the two resilient elements.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DESCRIPTION OF THE CURRENT EMBODIMENT

Overview.

Figures 1, 2:
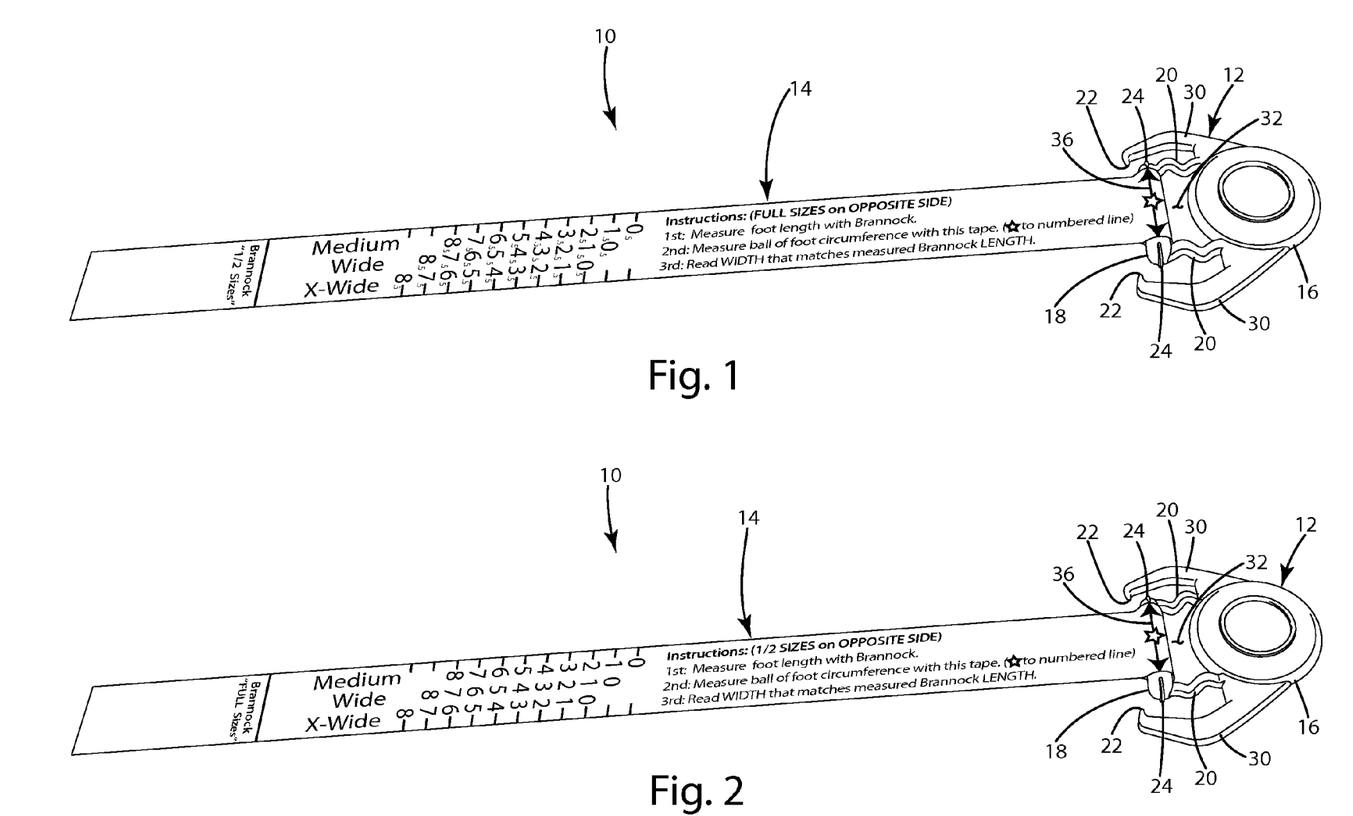
FIG. 1 is a top perspective view of an anthropometric measuring device in accordance with the present invention.
FIG. 2 is a bottom perspective view of the measuring device.

An anthropometric measuring device in accordance with an embodiment of the present invention is shown in FIGS. 1 and 2. The measuring device 10 generally includes a one-piece handle 12 and a measuring tape 14. In use, the measuring device 10 is intended to provide uniform measurements by allowing measurements to be taken with the measuring tape 14 held under uniform tension. The handle 12 includes a main body 16 that can be held by the user and an anchor portion 18 on which the measuring tape 14 is secured. The anchor portion 18 is joined to the main body 16 by one or more resilient elements 20. The resilient elements 20 are configured to undergo controlled deformation when the measuring tape 14 is placed under tension (See FIG. 3). The handle 12 includes a fixed reference 22 carried by the main body 16 and a movable reference 24 carried by the anchor portion 18. The fixed reference 22 and the movable reference 24 are arranged to align when the measuring tape 14 is under proper tension. The fixed reference 22 may also be used as a reference for taking measurements from the measuring tape 14, thereby allowing a user to look at a single reference point to ensure proper tension and to take measurements.

Figure 4:
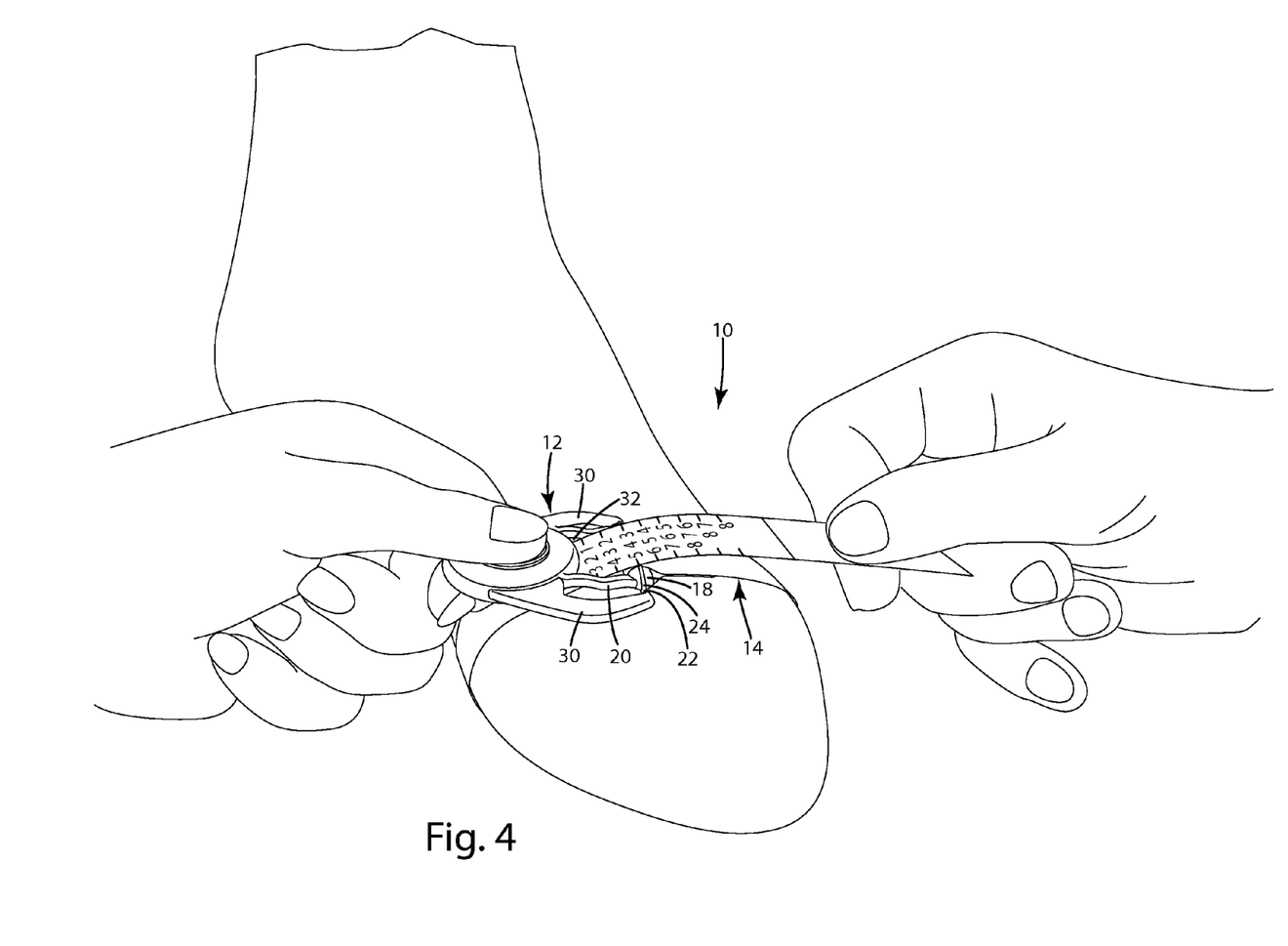
FIG. 4 is a perspective view showing the device in use around a child's foot.
Figure 5:
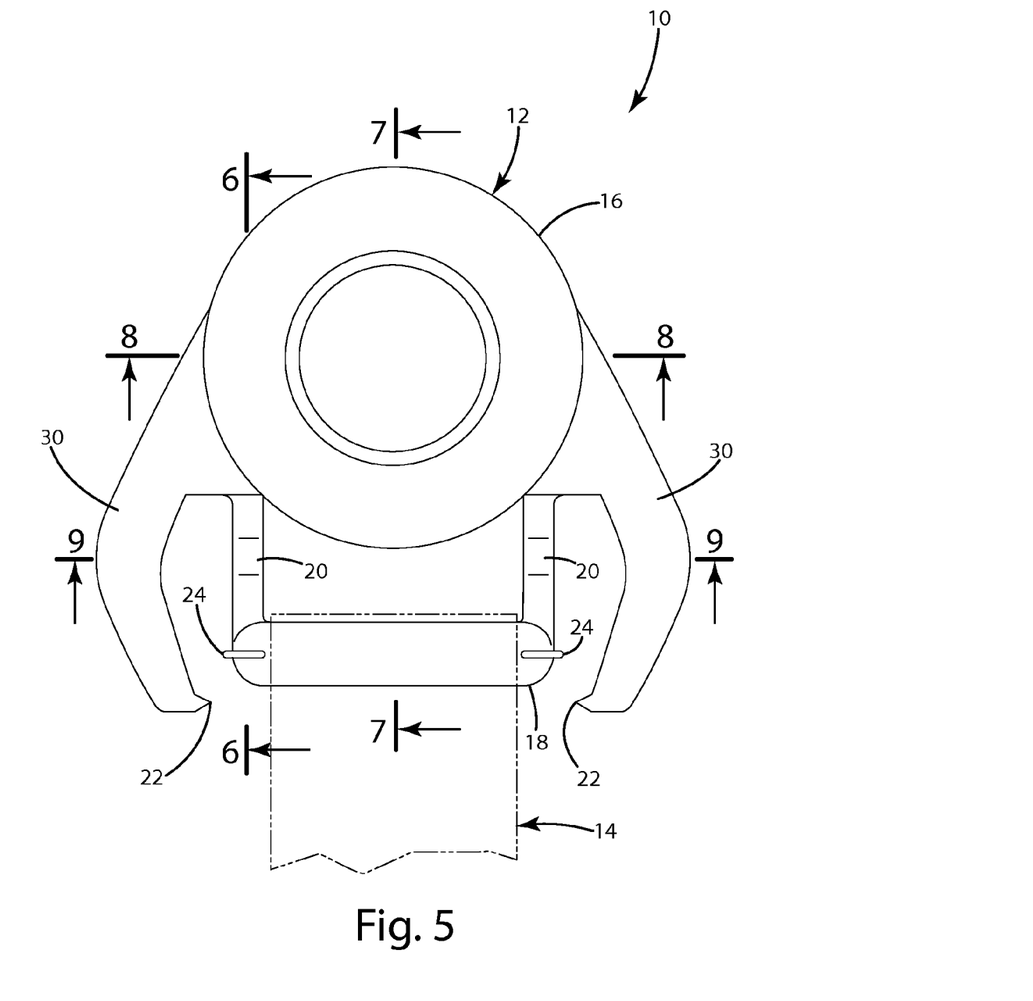
FIG. 5 is a top plan view of a portion of the device.

The present invention is described in the context of a measuring device 10 configured to measure a human foot to determine appropriate shoe width (See FIG. 4). In this context, the measuring device 10 includes a plurality of graduations and markings that can provide shoe width when shoe size (i.e. length) is already known. In the illustrated embodiment, the graduations and markings are a function of the size of the interior of the forefoot of the shoe, which in turn is a function of the last used to manufacture the shoe. A single measuring device may be used with a variety of different shoes if the different shoes share sufficiently common last sizes. In applications where last sizes are not sufficiently common from shoe to shoe, it may be desirable to provide different measuring devices for the different shoes. As an alternative to providing entirely different measuring devices, it may be desirable to provide a single handle with a plurality of replaceable measuring tapes, where the graduations and markings on each alternative measuring tape correspond to a different shoe. For example, each alternative measuring tape may terminate in a clip that can be removably fitted to the anchor bar.

Although the present invention is described in the context of a device for determining shoe width, the present invention may be readily adapted for use in taking other types of measurements under uniform tension. In different applications, the length of the measuring tape, the graduations/markings on the measuring tape and/or the resiliency of the resilient element(s) may be varied. For example, the present invention may be readily adapted for measuring chest circumference to determine coat or shirt size, or for measuring waist circumference to determine pant waist size. In these alternative embodiments, the measuring tape may be extended, the graduations/markings may be replaced with standard inch graduations/markings and the resilient elements may be tuned to the appropriate tension. The present invention may also be used in non-anthropometric measurements where it is desirable to take measurements with the measuring tape under uniform tension. For example, the measuring device may be useful in measuring the circumference of a compressible item or in measuring the circumference of a bundle of items in which the bundle may compress under load.

Various Embodiments

As noted above, the measuring device 10 of FIGS. 1 and 2 generally includes a handle 12 and a measuring tape 14. In this embodiment, the handle 12 is disposed on one end of the measuring device 10 and is intended to provide a structure that can be held by the user while a measurement is being taken. The handle 12 may vary from application to application in size, shape and configuration. In the illustrated embodiment, the handle 12 includes a main body 16, an anchor portion 18 and a pair of resilient elements 20. The shape of the main body 16 may vary from application to application. However, in the illustrated embodiment, the main body 16 is generally disc-shaped and has a pair of arms 30 that extend out to provide a pair of fixed references 22 disposed on opposite sides of the anchor portion 18 (See FIGS. 5-9). In this embodiment, the arms 30 terminate in arrows or pointers that define the fixed references 22. As can be seen, these arrows or pointers are directed at the measuring tape 14 from opposite sides. The use of opposed fixed references 22 makes it easier to read the tension measurement and the width measurement, and helps to ensure that the measuring tape 14 is not being pulled on an angle, which might affect the ability of the device 10 to ensure uniform tension. For example, if both sets of movable references 24 and fixed references 22 do not align simultaneously, then the measuring tape is likely being pulled at an angle and the tension measurement may not be accurate. Although the illustrated fixed references 22 are arrows or pointers defined by the shape of the arms 30, the fixed reference 22 may be essentially any element capable of function as a reference, such as any type of protrusion, recess, embossment, debossment or other contour or shape changed. The fixed reference 22 need not, however, be defined by the shape of the arms 30, but instead may be defined by printed matter, color variations or other types of visually perceptible references. As case be seen, the arms 30 are configured so that they functionally equally from both sides of the measuring device 10, thereby allowing them to function with graduations/marking on either side of the measuring tape 14. Although the illustrated embodiment includes a pair of opposed fixed references 22, the measuring device 10 may alternatively include a different number of fixed references. For example, the measuring device 10 may include only a single fixed reference, such as only one of the two arms 30. As another example, the device 10 may include more than two fixed references, such as four fixed references arranged so that there are two fixed references used with each side of the measuring tape 14. In this embodiment, the arms 30 are configured to provide a small gap (e.g. about 1 mm) between the fixed references 22 and the movable references 24. This gap will allow limited lateral movement between the anchor portion 18 and the arms 30 without the parts interfering with one another. Although the illustrated embodiment includes a gap of about 1 mm, the gap may be larger or smaller in alternative embodiments.

In the illustrated embodiment, the measuring tape 14 is joined to the handle 12 at the anchor portion 18. In the illustrated embodiment, the anchor portion 18 is a bar or similar structure to which the measuring tape 14 is attached. In this embodiment, the measuring tape 12 is attached by wrapping it around the anchor portion 18 and securing it back against itself, for example, with an adhesive or with mechanical fasteners (See FIG. 7). As shown, the length of the anchor portion 18 is approximately equal to the width of the measuring tape 14, but its length may be different, such as wider. In this embodiment, handle 12 includes two movable references 24 that are carried by the anchor portion 18. More specifically, as shown, arrow or pointer-shaped protrusions may extend from opposite ends of the anchor portion 18. Although the illustrated embodiment includes a pair of opposed movable references 24, the measuring device 10 may alternatively include a different number of movable references. For example, the measuring device 10 may include only a single movable reference, such as a protrusion extending from only one end of the anchor portion 18. As another example, the device 10 may include more than two movable references, such as four movable references arranged so that there are two movable references used with each side of the measuring tape 14. Although the illustrated movable references 24 are arrows or pointers defined by the shape of the ends of the anchor portion 18, the movable references 24 may be essentially any element capable of function as a reference, such as any type of protrusion, recess, embossment, debossment or other contour or shape changed. The movable reference 24 may alternatively be defined by printed matter, color variations or other types of visually perceptible references.

As noted above, the anchor portion 18 is secured to the main body 16 by one or more resilient elements. The resilient element(s) allow the anchor portion 18 to move increasingly farther away from the main body 16 as the tension on the measuring tape 14 increases. The design and configuration of the resilient element(s) may vary from application to application. In the illustrated embodiment, the anchor portion 18 is joined to the main body 16 by a pair of resilient elements 20. The number of resilient members may, however, vary from application to application. As shown, the resilient elements 20 of this embodiment extend essentially perpendicular to the length of the anchor portion 18 and attach the main body 16 to opposite ends of the anchor portion 18 (See FIGS. 6 and 7). In this embodiment, each resilient element 20 is non-liner in a direction that allows the resilient element 20 to be increasingly straightened when subjected to increasing load. As a result, the resilient element 20 is effectively elongated in a direction parallel to the direction of the force applied to the measuring tape 14. In use, increased force results in increased straightening and increased elongation of the resilient elements 20. This allows the anchor portion 18 and consequently the movable references 24 to move increasingly farther away from the main body 16 with increased force. The design and configuration of the resilient elements 20 is such that the movable references 24 come into alignment with the fixed references 22 when the proper tension or force is applied to the measuring tape 14 in the proper direction. In the illustrated embodiment, the resilient elements 20 are generally sinusoidal, thereby allowing significant movement of the anchor portion 18 away from the main body 16 through bending action of the resilient elements 20. In typical applications, it is desirable for the resilient elements 20 to be configured so that the anticipated forces will not be sufficient to move the resilient elements 20 outside of their elastic deformation range. This allows the resilient element to return essentially to its original shape after use and provides uniformity of result during repeated uses. If the resilient elements 20 are subjected to sufficient force to cause plastic deformation, the resilient elements 20 will be unable to return to their original shape when the force is removed and the results of sequential measurements may not be uniform. Although the resilient elements 20 may be configured to provide movement of the anchor portion 18 through resilient bending deformation, the resilient elements 20 may additionally or alternatively provide movement through resilient stretching. For example, the resilient elements 20 may be linear and they may undergo longitudinal stretching when the measuring tape 14 is subjected to sufficient force.

In the illustrated embodiment, the main body 16, anchor portion 18 and resilient elements 20 cooperatively define a loop 32 capable of receiving the measuring tape 14 during measurements (as described in more detail below). The loop 32 allows the operative portion of the measuring tape 14 to extend over the fixed end of the measuring tape 14. This in turn allows the width measurement to be taken using the fixed references 22.

The handle 12 may be manufactured using essentially any suitable techniques and apparatus. For example, the handle 12 may be injection molded from a suitable plastic or other polymer. Examples of suitable materials may include: TPU, PET, polypropylene, vinyl, PVC, polycarbonate. In the illustrated embodiment, the handle 12 is injection molded from Pebax® polyether block amide or other materials with similar elastic properties. The handle may be manufactured from other materials, such as metal or other materials having sufficient elastic properties. For example, the handle may be stamped in one piece from sheet metal. The resilient arms may be formed into a non-linear configuration (e.g. sinusoidal or curved) as an integral part of the stamping operation.

In the illustrated embodiment, the measuring device 10 includes one set of fixed references 22 and one set of movable references 24. If desired, the measuring device 10 may alternatively include multiple sets of fixed references and/or movable references. For example, in applications where it may be desirable to take measurements under different amounts of tension, there may be a separate set of fixed references for each alternative tension or there may be a separate set of movable references for each alternative tension. Multiple fixed references may be provided by including a plurality of pointers or arrows (or other visual indicia) at different locations along the arms 30. Multiple movable references may be provided by widening opposite ends of the anchor bar 18, and including a plurality of pointers or arrows (or other visual indicia) at different locations along the ends of the anchor bar 18. In some applications, it may be desirable to include multiple fixed references and multiple movable references, which can further increase the available tension options.

As noted above, the measuring device 10 includes a measuring tape 14. The measuring tape 14 may be essentially any flexible structure that is of sufficient length to perform the desired measurements. For example, the measuring tape 14 may be a length or ribbon of paper, cloth, fabric, plastic (e.g. vinyl), fiberglass or even metal. In the illustrated embodiment, the measuring tape 14 is of a length sufficient to extend around the circumference of a foot and provide enough material from to grip and pull the measuring tape 14.

In the illustrated embodiment, the measuring tape 14 includes graduations and markings on both major surfaces. More specifically, the graduations/marking for full sizes (e.g. 0, 1, 2, 3, 4, 5, 6, 7 and 8) are positioned on one side of the measuring tape 14 and graduations for half sizes (e.g. 0.5, 1.5, 2.5, 3.5, 4.5, 5.5, 6.5, 7.5 and 8.5) are positioned on the opposite side (Compare FIGS. 1 and 2). This is not strictly necessary and the graduations/marking for full and half sizes may be located on the same surface of the measuring tape 14. Although the configuration of graduations and markings may vary from application to application, in the illustrated embodiment, each side of the measuring tape includes a separate set of graduations along each lateral edge and a separate set of markings for each possible shoe width. The markings for the different shoe widths are offset from each other in correspondence with the actual variations in shoe widths. In this embodiment, the spacing between the markings is about 5 mm, but the spacing may vary from application to application depending at least in part on what is being measured. If desired, the markings for different shoe widths may be presented in different colors to facilitate use. As noted above, the graduations and markings are a function of the size of the interior of the forefoot of the shoe, which in turn is a function of the last used to manufacture the shoe. A single measuring device may be used with a variety of different shoes if the different shoes share sufficiently common last sizes. If not, it may be desirable to provide different measuring devices for the different shoes or to provide a single handle with a plurality of replaceable measuring tapes. Although the illustrated embodiment includes graduations in the form of line segments and markings in the form of printed numbers associated with the graduation, the graduations and/or markings may vary in alternative applications. For example, in some applications, the line segments may be replaced by other forms of visual indicia. In some applications, markings may be provided without separate graduations. In such applications, the markings may perform the dual-functions of graduations and markings. In other applications, graduations may be provided without markings.

Figure 3:
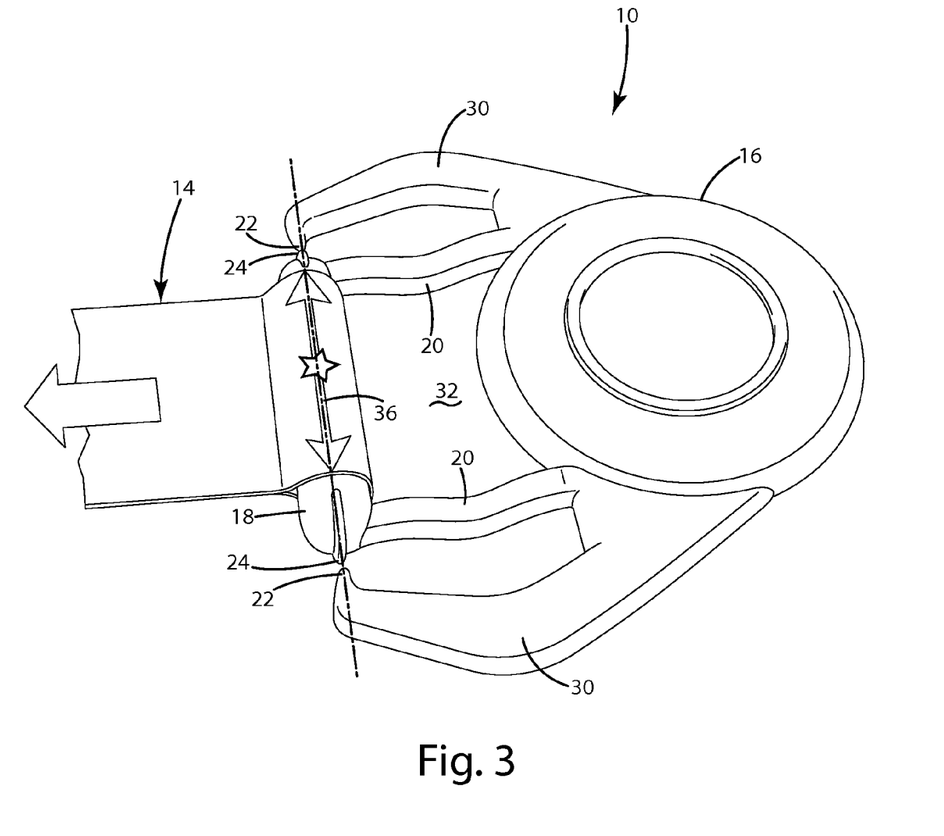
FIG. 3 is a perspective view of a portion of the device with measuring tape under tension and the resilient members extended.

To facilitate proper assembly of the measuring tape 14 to the handle 12, the measuring tape 15 may also include a baseline marking 36 (See FIG. 3). The baseline marking 36 may be used to ensure that the measuring tape 14 is properly positioned with respect to the anchor portion 18 so that the graduations and markings are at the correct distance from the movable references 24. To properly install the measuring tape 14, the measuring tape 14 may be wrapped around and secured back onto itself with the baseline marking 36 in alignment with the movable references 24.

Use of Measuring Device.

The measuring device 10 is intended for use in measuring foot circumference to determine shoe width. To use the measuring device 10, a measuring device is used to determine foot size (i.e. foot length). This may be done using a conventional Brannock device or by any other suitable measuring device, such as a measuring tape or ruler. It should be noted that the measuring tape 14 of the illustrated embodiment includes graduations/markings for full sizes on one side and for half sizes on the other. This was done primarily as an expedient so that the graduations/markings can be spaced out and more easily read. If desired, all of the graduations/marking may be disposed on one side of the measuring tape 14.

Once the foot length is determined, the measuring tape 14 is wrapped around the ball of the foot (See FIG. 4). Before doing so, the measuring device 10 should be oriented so that the appropriate side of the measuring tape 14 is facing outwardly. More specifically, if the foot being measures has a foot length that is a full size, the surface of the measuring device 14 bearing the full-size graduations/markings should be facing out (See FIG. 2). Alternatively, if the foot being measures has a foot length that is a half size, the surface of the measuring device 14 bearing the half-size graduations/markings should be facing out (See FIG. 1). The free end of the measuring tape 14 is fed through the loop 32 defined by the main body 16, the anchor portion 18 and the resilient elements 20. With the handle 12 in one hand and the free end of the measuring tape 14 in the other, the user pulls on the free end of the measuring tape 14 to apply tension. The user applies an increasing amount of tension until the movable reference 24 comes into alignment with the fixed reference 22. In the illustrated embodiment, the measuring tape 14 is pulled until both movable references 24 are simultaneously in alignment with both fixed references 22. If the references do not align simultaneously, it will likely be helpful to adjust the direction in which the measuring tape 14 is being pulled until both resilient elements 20 are under approximately equal load.

When the movable references 24 and fixed references 22 are aligned, the measuring tape 14 is under proper tension and the width measurement can be taken. In this embodiment, the fixed references 22 are used in combination with the graduations/marking on the measuring tape 14 to determine shoe width. More specifically, the measurement is taken by visually determine which measuring tape 14 graduation associated with the predetermined foot size is aligned with the fixed reference. For example, if the predetermined size is 8, the width is measured by determining whether the "8" from the medium scale, wide scale or extra wide scale is aligned with the fixed reference.

Select Alternative Embodiments

Figure 6:
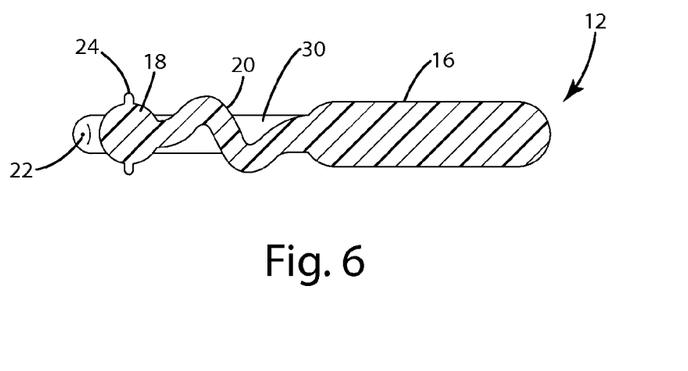
FIG. 6 is a sectional view of the device taken along line 6-6 of FIG. 5.
Figure 7:
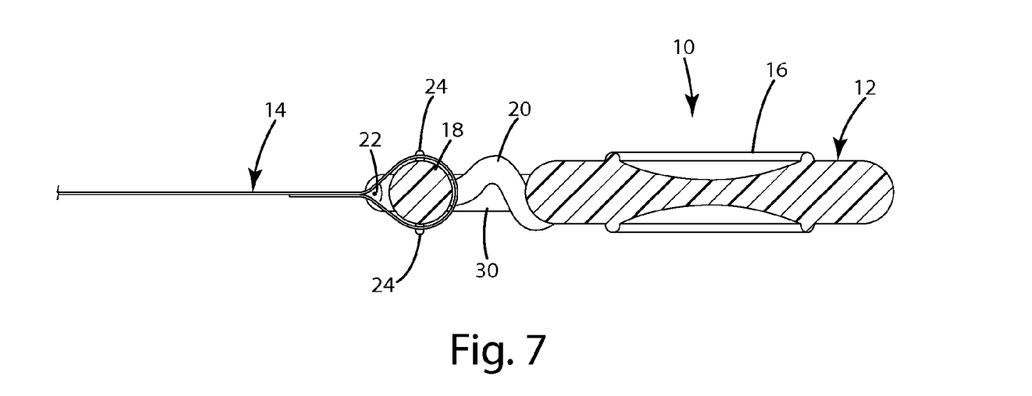
FIG. 7 is a sectional view of the device taken along line 7-7 of FIG. 5.
Figure 8:
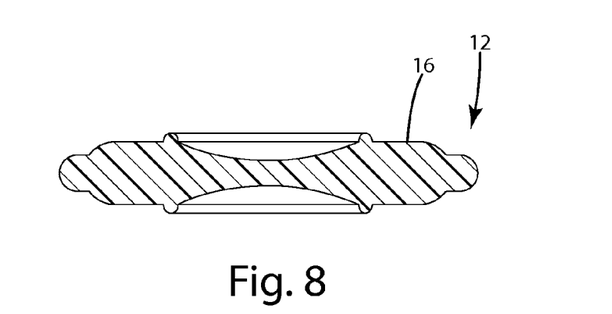
FIG. 8 is a sectional view of the device taken along line 8-8 of FIG. 5.
Figure 9:
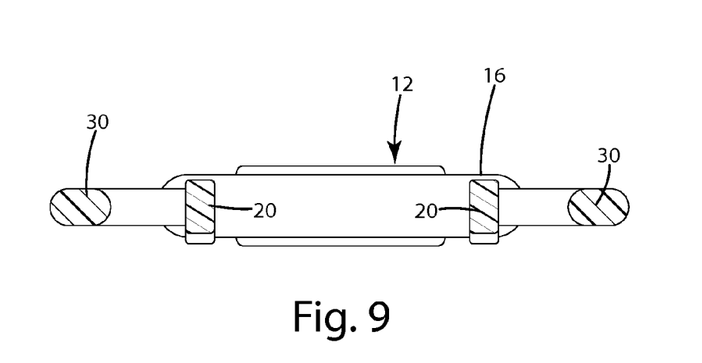
FIG. 9 is a sectional view of the device taken along line 9-9 of FIG. 5.
Figure 10:
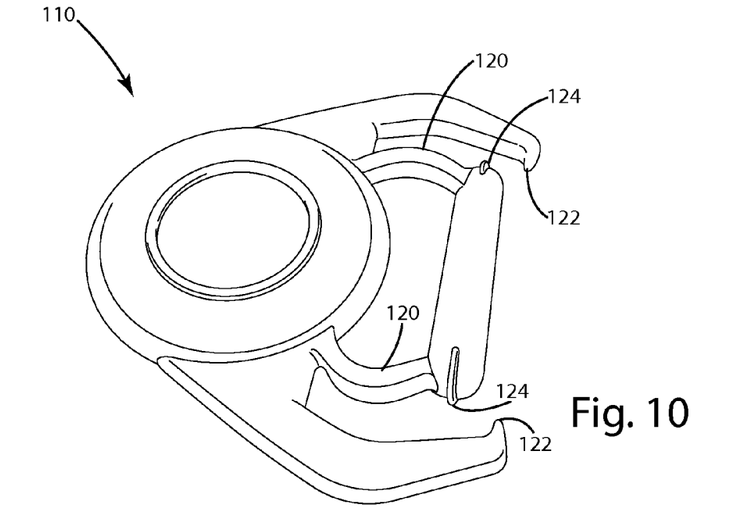
FIG. 10 is a perspective view of an alternative device having alternative resilient members.

As noted above, the resilient elements 20 of the embodiment of FIGS. 1-9 are generally sinusoidal in shape, which is perhaps best shown in FIGS. 6 and 7. The shape of the resilient elements may, however, vary from application to application. For example, in application where it is desirable to facilitate movement of the anchor portion 18 primarily through bending deformation, the resilient elements may have any of a wide variety of nonlinear shapes in the longitudinal direction. FIG. 10 shows and alternative measuring device 110 in which the resilient elements 120 are generally "C"-shaped and in the relaxed state bend outwardly away from one another. When placed under tension, the "C"-shaped resilient elements 120 straighten in proportion to the applied force, thereby increasing the effective length of the resilient elements 120 and allowing the movable reference 24 to move toward the fixed references 22. Although this alternative embodiment includes resilient elements that undergo elastic deformation primarily through bending, in other alternative embodiments, the elastic deformation may result more significantly from stretching rather than bending.

Figure 11:
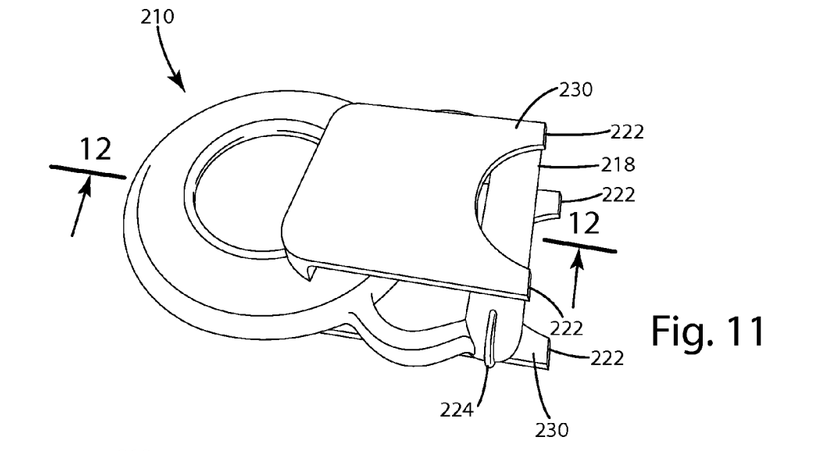
FIG. 11 is a perspective view of an alternative device having alternative fixed indicators.
Figure 12:
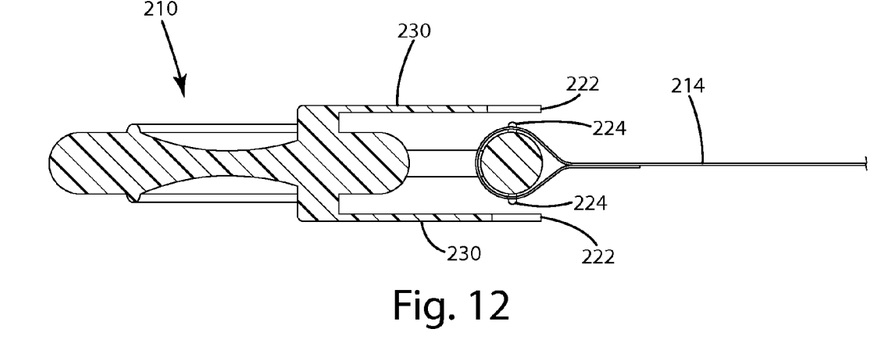
FIG. 12 is a section view of the alternative device of FIG. 11 taken along line 12-12 of FIG. 11.
Figure 13:
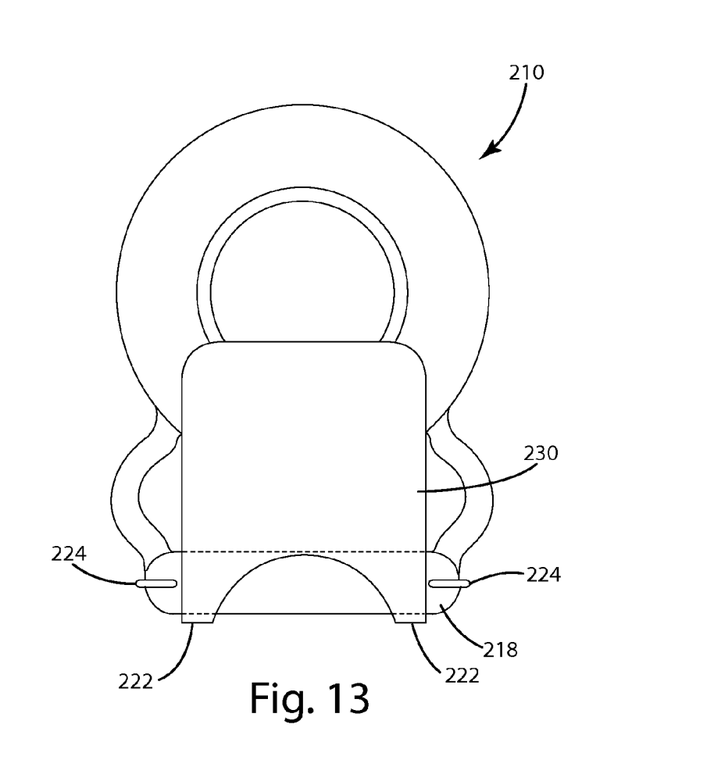
FIG. 13 is a top plan view of the alternative device of FIG. 11.

Another alternative embodiment is shown in FIG. 11-13. In this embodiment, the measuring device 210 includes arms 230 that extend above and below the measuring tape 214 rather than to opposite sides of the measuring tape 214. The fixed references 222 may be defined by the ends of the arms 230. For example, proper tension may be achieved applying sufficient force to cause the movable references 224 to align with the outermost ends of the arms 230. However, the arms 230 may include other types of references (or indicator), if desired. The center portion of the arms 230 may be recessed to make it easier to read the graduations and markings on the measuring tape 214. As perhaps best shown in FIG. 12, the arms 230 may be spaced apart from anchor bar 218 to provide a relatively narrow gap. The size of the gap may vary and, in some applications, may be eliminated. In applications where graduations/markings are provided on only one side of the measuring tape 214, the arm 230 associated with the unmarked side of the measuring tape 214 may be eliminated. The size, shape and configuration of arms 230 are merely exemplary. In alternative embodiments, the size, shape and configuration of the arms 230 may vary.

Figure 14:
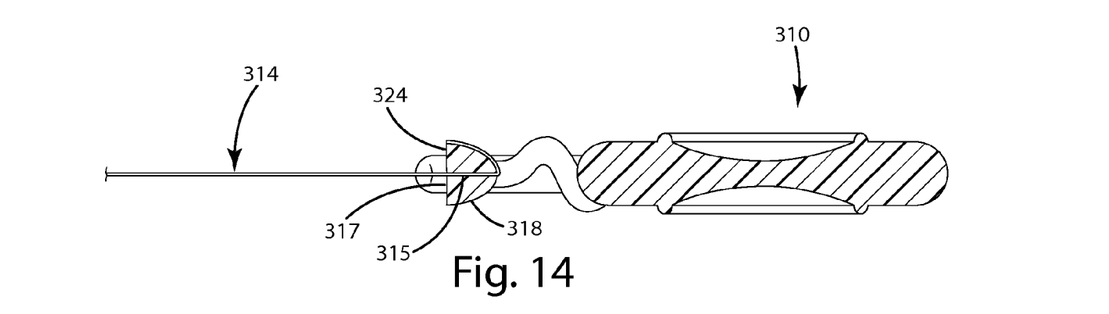
FIG. 14 is a sectional view showing a device with a first alternative anchor bar.
Figure 15:
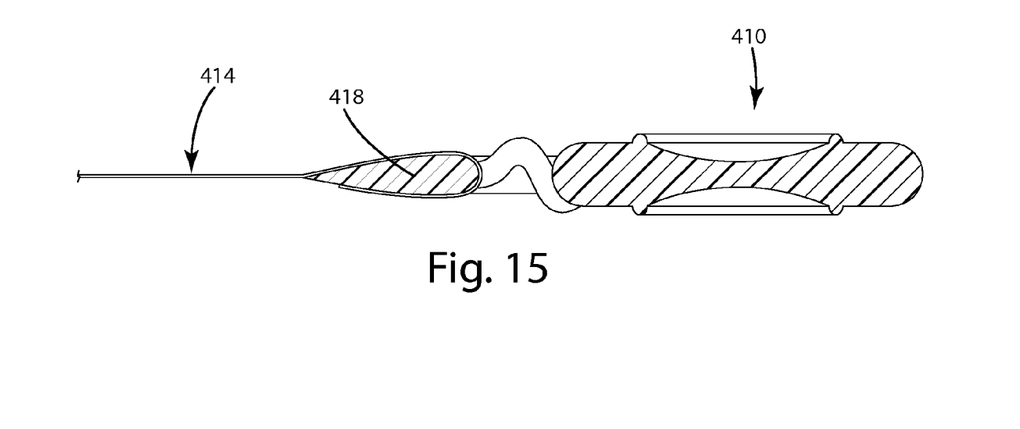
FIG. 15 is a sectional view showing a device with a second alternative anchor bar.

In the embodiment of FIGS. 1-6, the measuring tape 14 is secured to the handle 12 by wrapping it around the anchor portion 18 and securing it back onto itself. Alternatively configurations are shown in FIGS. 14 and 15. In FIG. 14, the measuring device 310 includes a measuring tape 314 that is fitted through a slot 315 in the anchor portion 318. The measuring tape 314 may be cemented or otherwise secured to the anchor portion 318. Although the measuring tape 314 is cemented to the anchor portion 318 in the embodiment, it may alternative be secured back onto itself. In the illustrated embodiment, the flat outer edge 317 of the anchor portion 318 may be used a baseline marking (or "zero point") for ensuring that the measuring tape 314 is secured to the anchor portion 318 in the correct position. The outer edge 317 may define and/or be aligned with the movable reference(s) 324. The cross-sectional shape of the anchor portion 318 may vary from application to application as desired. For example, the anchor portion 318 may be round in cross section and the slot 315 may be defined along the diameter of the round anchor portion.

In FIG. 15, the measuring device 410 includes an anchor portion 418 that has reduced thickness and is tapered toward its outer end. The measuring tape 414 may be wrapped partially around and cemented or otherwise secured to the anchor portion 418. Although the measuring tape 414 is cemented to the anchor portion 418 in the embodiment, it may alternative be secured back onto itself. In this embodiment, the cross section of the anchor portion 418 is thinner and has a significant taper. This alternative cross sectional shape decreases the offset between the foot and the measuring tape 414, which may improve the accuracy of measurements.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. An anthropometric measuring device for taking measurements under a defined force comprising:
    a one-piece handle including a fixed portion, a movable portion and a resilient portion joining said fixed portion to said movable portion, said fixed portion, said movable portion and said resilient portion being integrally formed, said handle including first and second fixed references associated with said fixed portion and a movable reference associated with said movable portion, said first fixed reference and said second fixed reference being disposed on opposite sides of said movable portion, said resilient portion including first and second resilient elements disposed toward opposite ends of said movable portion, said first and second resilient elements being configured to undergo elastic deformation that allows said movable reference to be moved into alignment with said first fixed reference and said second fixed reference under the defined force; and
    a measuring tape having at least one of graduations and markings, said measuring tape secured to said movable portion, wherein force applied to said measuring tape is transferred to said first and second resilient elements to cause elastic deformation of said resilient portion and movement of said movable portion with respect to said fixed portion, whereby said movable reference is movable into alignment with said first fixed reference and said second fixed reference by application of the defined force to said measuring tape in an appropriate direction.

2. The measuring device of claim 1 wherein said first and second fixed references provide references for determining proper application of force and a reference for taking a measurement based on said at least one of graduations and markings.

3. The measuring device of claim 1 wherein said first and second resilient elements having a non-linear shape in a direction associated with the defined force.

4. The measuring device of claim 3 wherein said movable portion includes an anchor bar with opposite ends, said resilient elements being joined to said anchor bar toward opposite ends, said resilient elements be spaced apart to accommodate said measuring tape therebetween.

5. The measuring device of claim 4 wherein said movable reference is a visual indication associated with said anchor bar.

6. The measuring device of claim 4 wherein said movable reference includes a first movable reference at one end of said anchor bar and a second movable reference at an opposite end of said anchor bar.

7. The measuring device of claim 6 wherein said fixed portion includes spaced apart first and second arms, said fixed portion including said first fixed reference on said first arm and said second fixed reference on said second arm.

8. The measuring device of claim 7 wherein said first fixed reference and said second fixed reference are disposed on opposite sides of said measuring tape.

9. The measuring device of claim 3 wherein said fixed portion, said movable portion and said resilient elements cooperatively define an opening of sufficient size to receive said measuring tape.

10. The measuring device of claim 1 wherein said measuring tape includes a zero marking to facilitate installation of said measuring tape on said movable portion.

11. The measuring device of claim 1 wherein said first and second resilient elements are sinusoidal.

12. A foot measuring device comprising:
a one-piece handle having a fixed portion, a movable portion and a resilient portion, said resilient portion joining said fixed portion to said movable portion, said handle including first and second fixed references associated with said fixed portion and a movable reference associated with said movable portion, said first and second fixed references being disposed on opposite sides of said movable portion, said resilient portion having first and second resilient elements deformable under force to allow relative movement between said movable portion and said fixed portion; and
a measuring tape having graduations and markings that associate a length size to a width size, said measuring tape secured to said movable portion, wherein force applied to said measuring tape is transferred to said movable portion and to said resilient portion, whereby pulling of said measuring tape may result in relative movement between said fixed portion and said movable portion;
wherein said resilient portion is configured to undergo elastic deformation that results in said movable reference moving into alignment with said first and second fixed references in response to the defined force being applied to said measuring tape in an appropriate direction.

13. The foot measuring device of claim 12 wherein said first and second fixed references provide a reference for determining proper application of force based on said movable reference and a reference for taking a width size measurement based on said graduations and markings.

14. The foot measuring device of claim 13 wherein at least one of said resilient elements has a non-linear shape in a direction associated with the defined force.

15. The foot measuring device of claim 13 wherein said first and second resilient elements have a non-linear shape in a direction associated with the defined force.

16. The foot measuring device of claim 15 wherein said movable portion includes an anchor bar with opposite ends, said first and second resilient elements being joined to said anchor bar toward opposite ends, said first and second resilient elements be spaced apart to accommodate said measuring tape therebetween.

17. The foot measuring device of claim 16 wherein said movable reference is a visual indication associated with said anchor bar.

18. The foot measuring device of claim 17 wherein said anchor bar includes a first movable reference at one end and a second movable reference at an opposite end.

19. The foot measuring device of claim 18 wherein said fixed portion includes spaced apart first and second arms, said first fixed reference being disposed on said first arm and said second fixed reference being disposed on said second arm, said first fixed reference and said second fixed reference disposed on opposite lateral sides of said measuring tape.

20. The foot measuring device of claim 15 wherein said fixed portion, said movable portion and said resilient elements cooperatively define an opening of sufficient size to receive said measuring tape.

21. The foot measuring device of claim 12 wherein said measuring tape include full-size graduations and markings on one surface and half-size graduations and markings on the other surface, said movable reference and said fixed references being visible from opposite sides of said handle.

22. A measuring device for determining shoe width size from foot circumference comprising:
a fixed portion having a pair of spaced apart fixed references;
a movable portion disposed between said pair of fixed references;
a resilient portion having a pair of resilient elements joining said fixed portion to said movable portion, said fixed portion, said movable portion and said resilient portion integrally formed as one piece, said resilient portion being capable of undergoing elastic deformation to allow relative movement between said fixed portion and said movable portion when a force is applied between said fixed portion and said movable portion; and
a measuring tape joined to said movable portion, whereby a pulling force applied to said measuring tape in a direction away from said fixed portion causes said movable portion to move away from said fixed portion, said resilient elements configured such that a movable reference that moves with said movable portion comes into alignment with said fixed references when proper tension for taking measurements has been applied to said measuring tape in an appropriate direction.

23. The measuring device of claim 22 wherein said movable portion includes an anchor bar and wherein said pair of resilient elements join opposite ends of said anchor bar to said fixed portion.

24. The measuring device of claim 23 wherein said fixed portion, said anchor bar and said resilient elements cooperatively define a loop through which a free end of said measuring tape may be passed while taking a measurement.

25. The measuring device of claim 24 wherein said fixed references cooperate with said movable reference to indicate a proper application of tension to said measuring tape and wherein said fixed references cooperate with at least one of graduation and marking on said measuring tape to provide a width size measurement.

* * * * *